United States Patent [19]

Polczynski

[11] Patent Number: 5,069,213

[45] Date of Patent: * Dec. 3, 1991

[54] OXIMETER SENSOR ASSEMBLY WITH INTEGRAL CABLE AND ENCODER

[75] Inventor: Mark H. Polczynski, Elm Grove, Wis.

[73] Assignee: Thor Technology Corporation, Milwaukee, Wis.

[*] Notice: The portion of the term of this patent subsequent to Oct. 23, 2007 has been disclaimed.

[21] Appl. No.: 452,719

[22] Filed: Dec. 19, 1989

Related U.S. Application Data

[63] Continuation-in-part of Ser. No. 188,217, Apr. 29, 1988, Pat. No. 4,964,408.

[51] Int. Cl.⁵ ............................................. A61B 5/00
[52] U.S. Cl. .................................... 128/633; 128/665
[58] Field of Search ........................ 128/633, 665, 666

[56] References Cited

U.S. PATENT DOCUMENTS

| | | |
|---|---|---|
| 3,536,545 | 10/1970 | Traynor et al. |
| 4,353,372 | 10/1982 | Ayer ..................................... 128/640 |
| 4,510,551 | 4/1985 | Brainard, II |
| 4,621,643 | 11/1986 | New, Jr. et al. |
| 4,653,498 | 3/1987 | New, Jr. et al. |
| 4,677,528 | 6/1987 | Miniet |
| 4,685,464 | 8/1987 | Goldberger et al. |
| 4,700,708 | 10/1987 | New, Jr. et al. |
| 4,726,382 | 2/1988 | Boehmer et al. |
| 4,770,179 | 9/1988 | New, Jr. et al. |
| 4,783,815 | 11/1988 | Buttner |
| 4,825,879 | 5/1989 | Tan et al. |
| 4,830,014 | 5/1989 | Goodman et al. |
| 4,865,038 | 9/1989 | Rich et al. ............................ 128/633 |
| 4,964,408 | 10/1990 | Hink et al. ............................ 128/633 |

OTHER PUBLICATIONS

*Anesthesiology News*, vol. 13, No. 7, Jul. 1987, pp. 1, 66, 68, 69.

*Primary Examiner*—Kyle L. Howell
*Assistant Examiner*—Kevin Pontius
*Attorney, Agent, or Firm*—Andrus, Sceales, Starke & Sawall

[57] ABSTRACT

An oximeter sensor assembly (40) includes a thin elongated flexible sheet-like strip (42) having an integral end portion (44) for flexibly wrapping at least partially around a human body part (26), a plurality of electrical conductors (46-50) on the strip, light emitting and receiving electrical components (28a, 30a) mounted on the strip on the end portion and electrically connected to the conductors, and encoding means provided by a pair of auxiliary conductors (202, 204) and resistance material (206) therebetween for providing signals to the oximeter indicative of the known wavelength of the light emitting electrical component for calibrating the oximeter.

10 Claims, 4 Drawing Sheets

OXIMETER SENSOR ASSEMBLY WITH INTEGRAL CABLE AND ENCODER

CROSS-REFERENCE TO RELATED APPLICATION

This application is a continuation-in-part of application Ser. No. 07/188,217, filed Apr. 29, 1988 now U.S. Pat. No. 4964408.

BACKGROUND AND SUMMARY

The invention arose during continuing development efforts directed to providing a low cost oximeter sensor assembly with integral cable, and particularly to improved calibration and encoding.

Oximeters are known in the art, and are used by anesthesiologists for continuous intraoperative noninvasive monitoring of arterial oxygen saturation of the patient under anesthesia, *Anesthesiology News*, Volume 13, Number 7, July 1987, pages 1, 66, 68 and 69, and also for neo-natal monitoring, and for various other uses. The oximeter provides a prewarning of hypoxia. A sensor having light emitting diodes and a light receiving element is placed around a finger tip, a toe, an ear lobe, the nose, etc. The effect of the patient's blood and its oxygen content on the intensity of light at a particular wavelength of light received by the light receiving element from the light emitting diodes give a measure of the oxygen content in the blood, U.S. Pat. Nos. 4,621,643, 4,653,498, 4,685,464, 4,700,708, 4,770,179, 4,825,879, 4,830,014, incorporated herein by reference.

The invention in the noted parent application provides an oximeter sensor assembly with integral cable. The assembly is characterized by low material cost, low assembly cost, suitability for high volume automated manufacturing as well as variable quantity manufacturing. The assembly provides a high degree of mechanical flexibility, and also offers full electromagnetic interference shielding if desired.

The invention of the noted parent application offers a significant commercial advantage in that it reduces cost by a factor of 7. This 7:1 cost advantage makes the sensor assembly disposable, which is deemed highly desirable.

The present invention provides a particularly simple and cost effective encoder on the substrate strip of the parent invention for calibration of the oximeter.

BRIEF DESCRIPTION OF THE DRAWINGS

Prior Art

Parent Application

Present Invention

DETAILED DESCRIPTION

Prior Art

Figures 1, 2, 3:
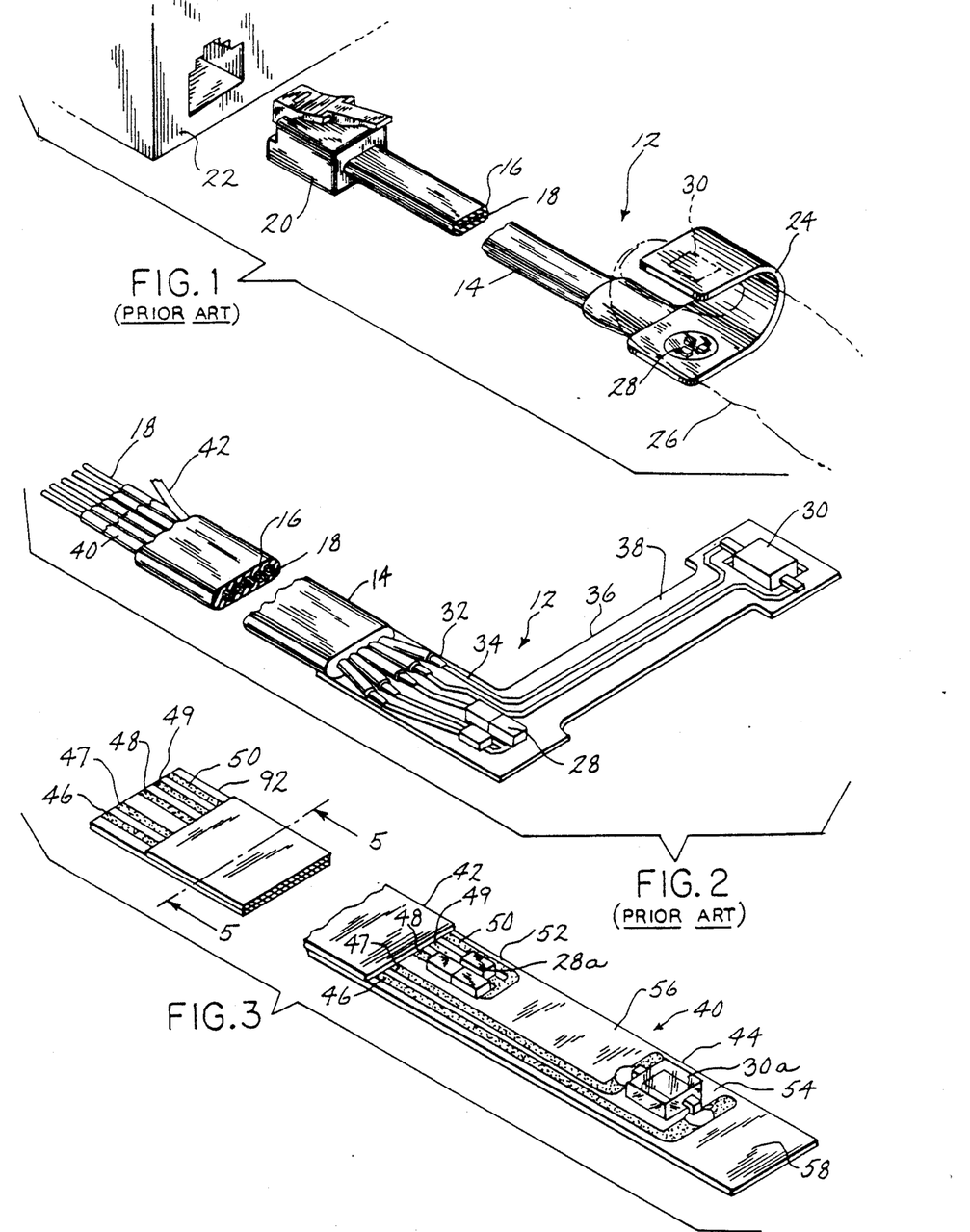
FIG. 1 is a perspective view of an oximeter sensor assembly known in the prior art.
FIG. 2 is a perspective view showing the inner construction of the assembly of FIG. 1.
FIG. 3 is a perspective view of an oximeter sensor assembly in accordance with the invention of noted parent application Ser. No. 07/188,217.

FIG. 1 shows an oximeter sensor assembly 12 having a cable 14 with an electrically insulating sheath 16 and a plurality of electrical conductors 18. The left end of the cable is connected by modular plug 20 to a patient adaptor plug 22 which is connected to an oximeter, for which further reference may be had to the above incorporated patents. The right end of the cable has a cover strap 24 which is flexibly wrapped at least partially around a finger tip 26 or other human body part. Electrical conductors 18 are connected to light emitting diodes 28 and to a light receiving electrical component 30. Light from LED's 28 passes upwardly through the finger to receiver 30. Blood oxygen content affects the light received at receiver 30, which is interpreted by the oximeter.

FIG. 2 shows the internal construction of the oximeter sensor assembly of FIG. 1. Conductors 18 are soldered at 32 to conductors 34 on electrically insulating substrate strip 36, to make connections to LED's 28 and light receiver 30. The electrical components and conductors on the substrate are covered by a thin transparent electrically insulating film 38 and then by cover strap 24. An electrically conductive shield 40 is around conductors 18 and has a shield contact connector 42 for grounding or the like connection to the oximeter, for shielding conductors 18 against electromagnetic interference, which can be a particular problem in the operating room.

The assembly of FIGS. 1 and 2 is expensive, both in material cost and in assembly cost. The assembly requires numerous manual operations.

Parent Application

FIG. 3 shows an oximeter sensor assembly 40 with integral cable 42 in accordance with the invention of the parent application. Cable 42 is a thin elongated flexible sheet-like multi-layer strip having an integral end portion 44 flexibly wrapping at least partially around a human body part, such as finger 26. The cable includes a plurality of electrical conductors 46, 47, 48, 49, 50. Light emitting diodes 28a and light receiving electrical component 30a are mounted on the cable and soldered or glued with electrically conductive adhesive to respective conductors to make electrical contact thereto. At least two of the conductors, and preferably three as shown at conductors 48, 49, 50, extend along end portion 44 to a first given area 52. In one embodiment, there are two LED's connected in series emitting in the red spectrum, and another LED connected in parallel therewith and emitting in the infrared spectrum, which is currently preferred in pulse oximeters, though other configurations are of course possible. Two of the conductors 46 and 47 extend along end portion 44 to a second given area 54 where light receiving electrical component 30a is mounted.

Figure 4:
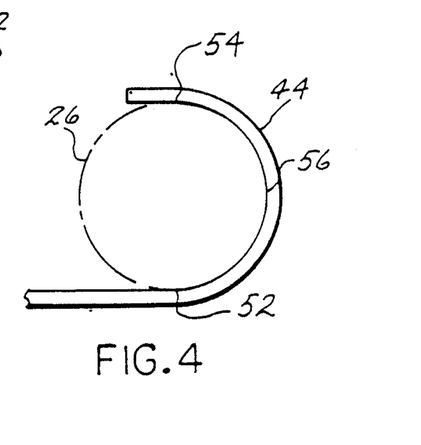
FIG. 4 is an end view showing an end of the assembly of FIGS. 1, 2 or 3 wrapped around a finger.

Areas 52 and 54 are spaced along end portion 44 and have an intermediate section 56 therebetween. The conductors and the electrical components are covered by a thin transparent electrically insulating film 58. Intermediate section 56 flexibly wraps at least partially around finger 26, FIG. 4, and is held thereon by tape, such that finger 26 is between areas 52 and 54 of end portion 44 of the cable and between light emitting electrical components 28a and light receiving electrical component 30a, such that light emitted from light emitting electrical components 28a travels through finger 26 and is received by light receiving electrical component 30a. Conductors 46–50 extend longitudinally along cable 42 and its integral end portion 44, and areas 52 and 54 are longitudinally spaced along end portion 44 such that end portion 44 is wrapped at least partially around finger 26 along a direction parallel to the longitudinal extension of the conductors. Cable end 44 may of course be wrapped around other body parts.

Figure 5:
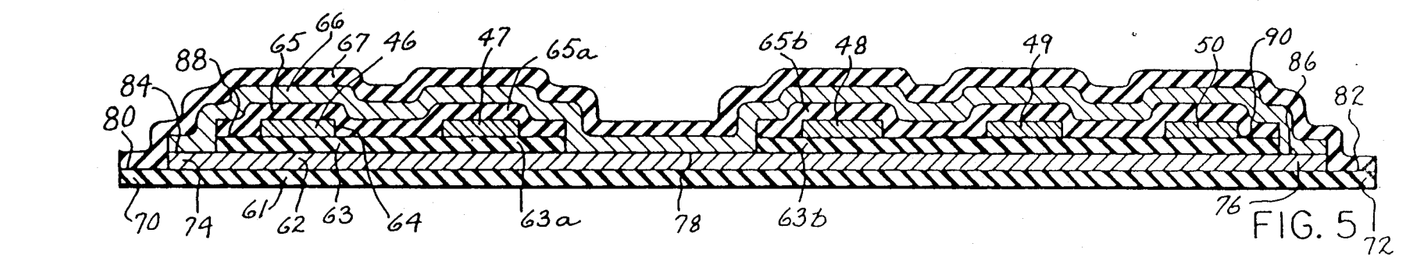
FIG. 5 is a sectional view taken along line 5—5 of FIG. 3.

FIG. 5 shows in cross section the preferred construction of the assembly of FIG. 3. The thickness of the assembly in FIGS. 3 and 5 is about five mils. The elevations in FIG. 5 are exaggerated for clarity of illustration. A first layer 61 is provided by a thin elongated flexible sheet-like electrically insulating strip. A second layer 62 is provided on the first layer by a thin elongated flexible sheet-like electrically conductive strip. A third layer 63 is provided on the second layer by a thin elongated flexible sheet-like electrically insulating strip. A fourth layer 64 is provided on the third layer by a plurality of electrical conductors. A fifth layer 65 is provided on the fourth layer by a thin elongated flexible sheet-like electrically insulating strip. A sixth layer 66 is provided on the fifth layer by a thin elongated flexible sheet-like electrically conductive strip. A seventh layer 67 is provided on the sixth layer by a thin elongated flexible sheet-like electrically insulating strip.

In making the structure of FIG. 5, an insulating substrate 61 is provided, followed by formation of conductive layer 62 by vacuum deposition, sputtering, printing, or by etching away metal on a previously metallized insulating substrate 61 to leave the lateral ends 70 and 72 of insulating substrate 61 exposed and the remainder of the substrate covered by metallization 62. Another electrically insulating layer 63 is then provided to cover layer 62, but leaving the lateral ends 74 and 76 of layer 62 exposed. Layer 63 is formed by left and right portions 63a and 63b having a longitudinal central gap 78 therebetween. Conductors 46–50 are then formed by vacuum deposition, sputtering, printing, or by etching away metallization on insulating strips 63a and 63b. Conductors 46–50 provide fourth layer 64. Conductors 46 and 47 are to the left lateral side of gap 78, and conductors 48, 49, 50 are to the right lateral side of gap 78. Insulating layer 65 is then provided to cover conductors 46–50. Layer 65 is formed by left and right portions 65a and 65b having longitudinal central gap 78 therebetween. Layers 65a and 65b extend to the edges of layers 63a and 63b. Conductive layer 66 is then formed over layer 65 and the exposed regions of layer 62 at the central gap 78, and extends to the edges of layer 62. Insulating layer 67 is then formed over layer 66 and extends to the edges of layer 61.

Layers 61 and 67 have lateral widths greater than layers 62 and 66 and extend laterally beyond layers 62 and 66. Layers 61 and 67 engage each other along their laterally outward edges at interfaces 80 and 82 and provide electrical insulation between the patient and the conductive layers 62 and 66. Layers 62 and 66 have lateral widths greater than layers 63 and 65 and extend laterally beyond layers 63 and 65. Layers 62 and 66 engage each other along their laterally outward edges at interfaces 84 and 86 and provide electromagnetic shielding of conductors 46–50. Layers 63 and 65 extend laterally beyond the lateral extent of the conductors and engage each other along their laterally outward edges at interfaces 88 and 90 and also engage each other in central gap 78. Gap 78 in layers 63 and 65 enables shield layers 62 and 66 to engage each other at such gap 78. The shield is thus around all the conductors, and a conductive shield is also provided around those conductors 46 and 47 to the left of gap 78, and a conductive shield is also provided around those conductors 48–50 to the right of gap 78.

Figure 6:
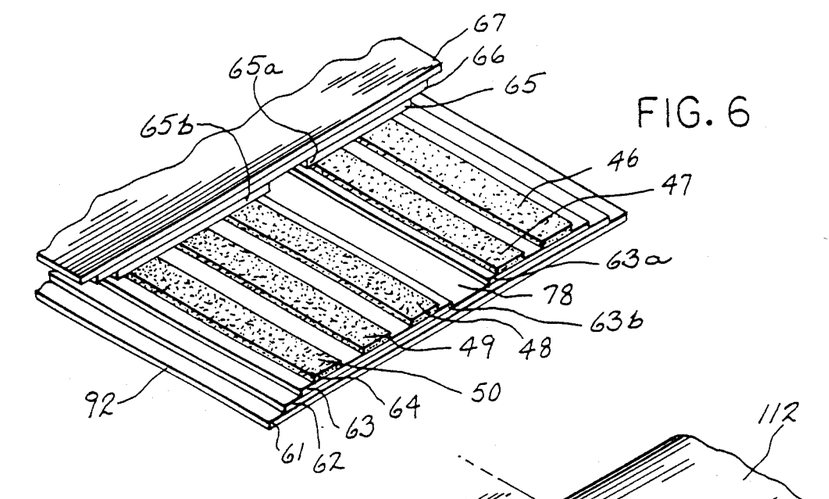
FIG. 6 is a perspective view of one longitudinal end of the assembly of FIG. 3.

The assembly has a longitudinal end 44, FIG. 3, with layers 61, 62, 63, 64 extending longitudinally beyond layers 65, 66, 67. Electrical components 28a and 30a are connected to this longitudinal end, and the components and the conductors are covered by the noted thin transparent electrically insulating film 58. This longitudinal end wraps around the patient's finger or other appendage. The other longitudinal end 92 of the assembly, FIGS. 3 and 6, has layers 61, 62, 63, 64 extending longitudinally beyond layers 65, 66, 67. Gap 78 in layer 63 extends longitudinally along the cable including along longitudinal end 92, but not along longitudinal end 44.

Figure 7:
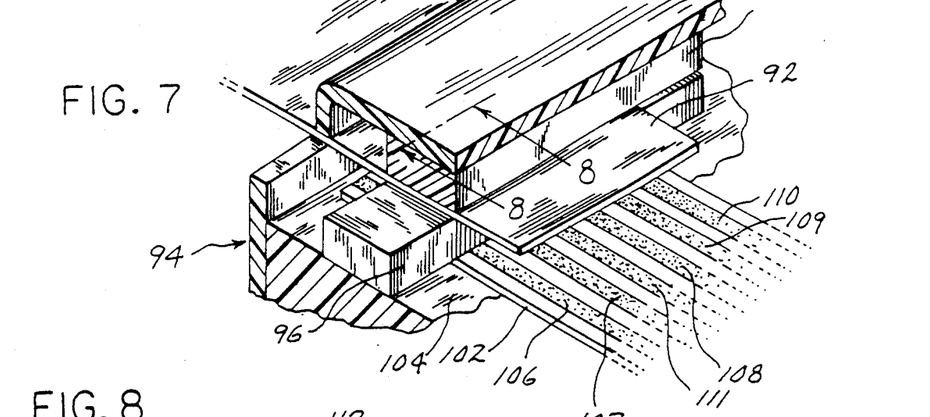
FIG. 7 is a perspective view showing connector structure for the assembly of FIG. 3.

A connection adaptor 94, FIG. 7, is provided for making electrical contact to conductors 46–50 and the conductive shield at longitudinal end 92 of the assembly. In FIG. 7, assembly end 92 is turned upside down from the view in FIG. 6 and makes contact with an elastomeric interconnect structure 96 formed by a plurality of thin electrically conductive sheets 98, FIG. 8, interleaved with a plurality of thin electrically insulating sheets 100. An electrically insulating strip 102 rests on base 104 of the connection adaptor and has a plurality of electrical conductors 106, 107, 108, 109, 110 thereon. Conductor/insulator interleaved interconnect structure 96 is on strip 102. Longitudinal end 92 of assembly 40 is on interconnect structure 96, and a lid or hinged cover 112 is closed to press pad 114 against longitudinal end 92 to clamp conductors 46–50 into electrical contact with interconnect structure 96, and in turn clamp interleaved structure 96 into electrical contact with conductors 106–110, with a clamping force applied perpendicularly to strips 92 and 102.

Figure 8:
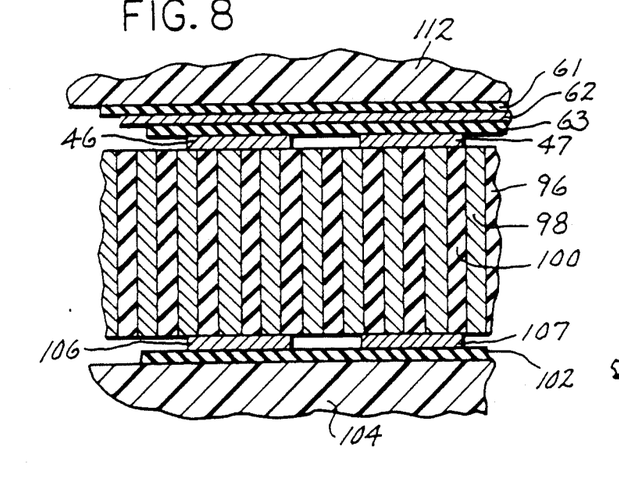
FIG. 8 is a sectional view taken along line 8—8 of FIG. 7.

As shown in FIG. 8, each of sheets 98 and 100 extends generally vertically and longitudinally parallel to the longitudinal extension of the conductors 46–50 and 106–110. The lateral width of each conductor sheet 98 and the lateral width of each insulator sheet 100 is less than the lateral width of each conductor 46–50 and 106–110 and is less than the lateral gap between such conductors. This permits some misalignment between the upper and lower sets of conductors 46-50 and 106-110 and ensures for example that conductor 46 will make contact to conductor 106 through at least one conductor sheet 98, and that at least one insulator sheet 100 will be laterally between conductor 46 and 47 to prevent shorting therebetween, and likewise to prevent shorting between conductors 106 and 107. Conductor 111 on strip 102 makes electrical contact through connector structure 96 to layer 62 at gap 78 to thus provide electrical contact to the shield. As noted above, the elevations and heights shown in the drawings are exaggerated for illustration purposes.

Figure 9:
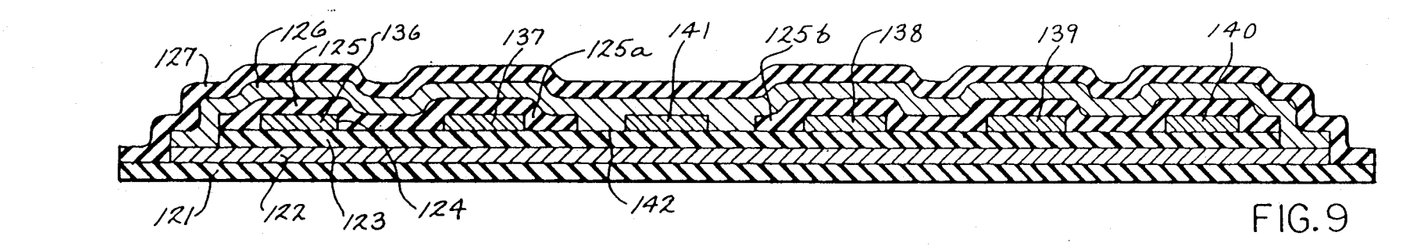
FIG. 9 is a sectional view of FIG. 5 and shows an alternate embodiment.

FIG. 9 shows an alternate embodiment with first through seventh layers 121, 122, 123, 124, 125, 26, 127, corresponding respectively to layers 61, 62, 3, 64, 65, 66, 67 of FIG. 5. Fourth layer 124 is provided by conductors 136, 137, 138, 139, 140, corresponding respectively to conductors 66, 67, 68, 69, 70 of FIG. 5. Third layer 123 is laterally continuous along its width, unlike third layer 63 in FIG. 5. A sixth central conductor 141 is formed during the same step when conductors 136–140 are formed. Fifth layer 125 is longitudinally split at gap 142 to form left lateral portion 125a to the left of gap 142, and to form right lateral portion 125b to the right of gap 142. Sixth layer 126 electrically contacts conductor 141 in gap 142. The balance of the structure of FIG. 9 is comparable to that of FIG. 5. Conductor 111 makes electrical contact through interconnect structure 96 to conductor 141 to provide electrical contact to the shield provided by layers 122 and 126.

Figure 10:
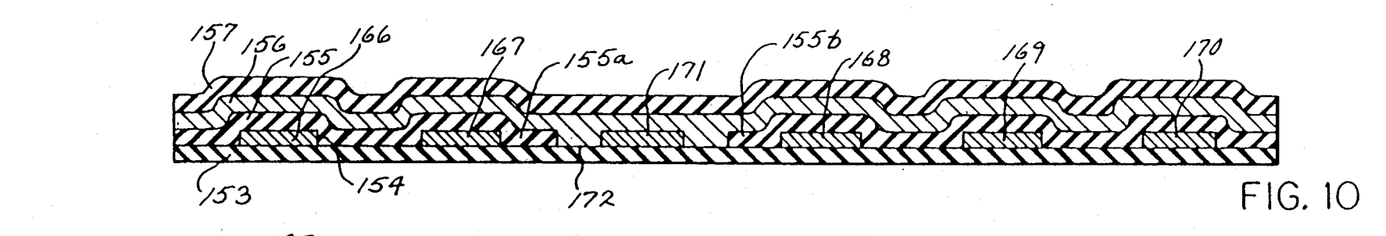
FIG. 10 is a sectional view of FIG. 5 and shows an alternate embodiment.

FIG. 10 shows an alternate embodiment using five layers 153, 154, 155, 156, 157, corresponding respectively to layers 123, 124, 125, 126, 127 of FIG. 9. Layer 154 is provided by conductors 166, 167, 168, 169, 170, 171, corresponding respectively to conductors 136, 137, 138, 139, 140, 141 of FIG. 9. Insulating layer 153 extends laterally continuously across and beneath conductors 166-171, comparably to insulator 123 in FIG. 9. Insulating layer 155 has a central longitudinal gap 172, forming a left lateral portion 155a to the left of gap 172, and a right lateral portion 155b to the right of gap 172, comparably to insulating layer 125 and gap 142 in FIG. 9. Conductor layer 156 covers insulating layer 155 and electrically contacts conductor 171 in gap 172. Insulator layer 157 covers conductor layer 156. Layer 156 provides a ground plane for use in those applications where full shielding is not necessary. Contact to the ground plane is provided through conductor 171, comparably to electrical contact to conductor 141 in FIG. 9.

Figure 11:
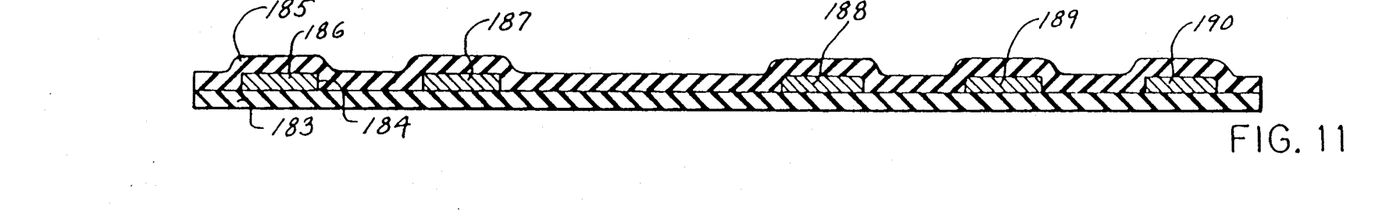
FIG. 11 is a sectional view of FIG. 5 and shows an alternate embodiment.

FIG. 11 shows an alternate embodiment using three layers 183, 184, 185, corresponding respectively to layers 63, 64, 65 of FIG. 5. Layers 183 and 185 are electrically insulating strips. Layer 184 is provided by electrical conductors 186, 187, 188, 189, 190, corresponding respectively to conductors 46, 47, 48, 49, 50 of FIG. 5. The structure of FIG. 11 is used in those applications not requiring a shield or a ground plane.

Further Prior Art

Pulse oximeter instruments are sensitive to the frequency and intensity of the light emitted and detected by the sensor's optoelectronic components. For some instruments, the exact frequency and intensity sensitivity characteristics of the particular sensor must be known. This is often done by measuring the characteristics of a sensor, and then coding the sensor in some way that allows the associated instrument to read the characteristics of the particular sensor and adjust its readings accordingly.

A common way to code a sensor is to attach a resistor to the sensor such that when the sensor is plugged into the instrument, the instrument can measure the value of the resistor. The value of the resistor for a particular sensor is selected in accordance with the optoelectronic characteristics of the sensor as measured at the time of testing. Electrical current through the resistor provides signals to the oximeter instrument indicative of the known wavelength and/or intensity of the light emitting electrical component for calibrating the oximeter.

New, Jr. et al U.S. Pat. No. 4,621,643 discloses a calibrated optical oximeter probe including a tape 50 having a photoelectric sensor 30 and first and second LEDs 10 and 20. A resistor 40 is mounted to tape 50 between sensor 30 and LED 10. Resistor 40 has an input lead wire 41 and is connected to ground wire G. LEDs 10 and 20 are selected from batches of LEDs with generally known wavelength characteristics. The exact wavelength characteristics of the specific LEDs 10, 20 chosen are determined through readily available metering means. Resistor 40 is then selected to have a resistance whose value is exactly specified by a table made available to the factory technician for this purpose, of all possible wavelength combinations which may be expected to be encountered from the available supplies of LEDs. New, Jr. et al shows at the top of column 6 a table as an example of how a single resistor 40 might be selected for any hypothetical combination of LEDs 10, 20 in a case where each has only two possible wavelengths. According to such table, a probe having such wavelength characteristics will be supplied at the factory with a resistor 40 of one, and only one, resistance value. The advantage in having a unique known resistance value incorporated into probe 1 is shown by reference to FIG. 4 of New, Jr. et al. Oximeter 60 contains a microprocessor 61, and a read only memory 62 and random access memory 63. The above noted table may be programmed into ROM 62 at the time oximeter 60 is fabricated. Current I from current source 69 is passed through resistor 40. The resulting voltage is passed through multiplexer 66 through comparator 65 to microprocessor 61. The microprocessor may be programmed to calculate the resistance of resistor 40 and thereafter to look up the wavelengths of LEDs 10, 20 from the above noted table in ROM 62. Microprocessor 61 is also programmed to itself recalibrate the optical comparison circuitry of oximeter 60 once the wavelengths of LEDs 10, 20 are known. It is thus not required to recalibrate by hand oximeter 60 for each new probe 1, nor, alternatively, to require that LEDs 10, 20 be of precisely standardized wavelengths.

Coding resistors typically constitute descrete components soldered into the sensor. This is costly, time consuming, and prone to defect. The present invention provides an alternative approach, which is particularly suited for use in combination with the sensor of the above noted parent application.

Present Invention

FIGS. 12-16 illustrate the present invention, and use like reference numerals from FIGS. 1-11 where appropriate to facilitate understanding. Cable 42 of sensor assembly 40 is modified to be widened at portion 200 to accommodate a pair of auxiliary conductors 202 and 204 extending longitudinally on end portion 92, in addition to primary conductors 46-50. Conductors 202 and 204 are formed on the substrate strip at the same time as conductors 46–50. Electrically resistive film material 206 is formed on the substrate strip laterally between auxiliary conductors 202 and 204, and provides an encoding resistor. The encoder provided by auxiliary conductors 202 and 204 and resistance 206 is especially well suited to the sensor configuration of the above noted parent application. Resistor 206 is directly printed onto the sensor using, for example, a polymer thick film resistive material. This overcomes problems encountered with prior coding resistors constituting discrete components soldered onto the sensor, which is costly, time consuming, and prone to defect.

Figure 12:
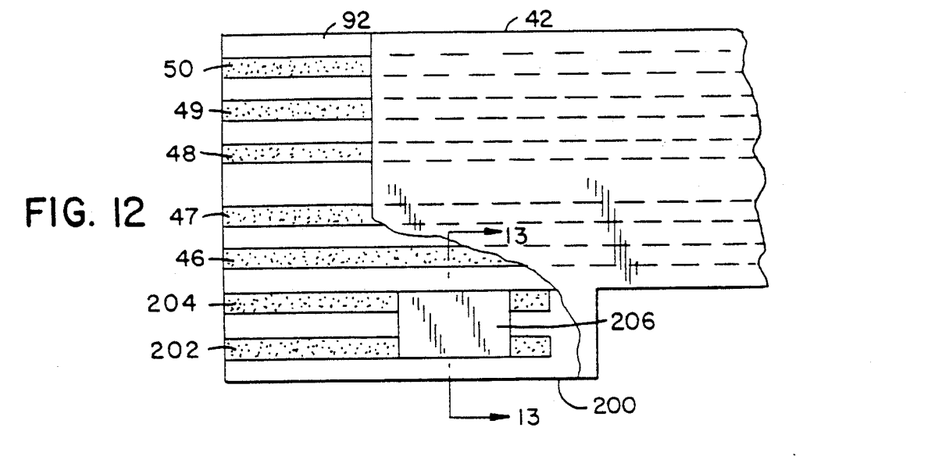
FIG. 12 is a top view of the left end portion of the oximeter sensor assembly of FIG. 3 modified in accordance with the present invention.
Figure 13:
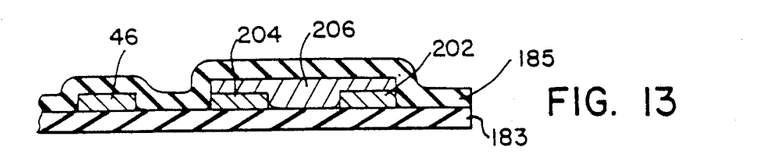
FIG. 13 is a sectional view taken along line 13—13 of FIG. 12.

The resistance value of resistor 206 is readily and variably controllable by varying the width of the resistor, the thickness of the resistor, the resistivity of the printed resistive material, and/or trimming. If the resistance value is set by varying the width of the resistor or the resistivity of the resistor material, then printing of the resistor should be done after optoelectronic characterization of the particular device. If, however, a printed resistor is trimmed to a desired value, printing of the resistor can take place earlier during the fabrication of the cable. The resistor can be trimmed by partial cutting or other configuring thereof to a desired resistance value.

Figure 14:
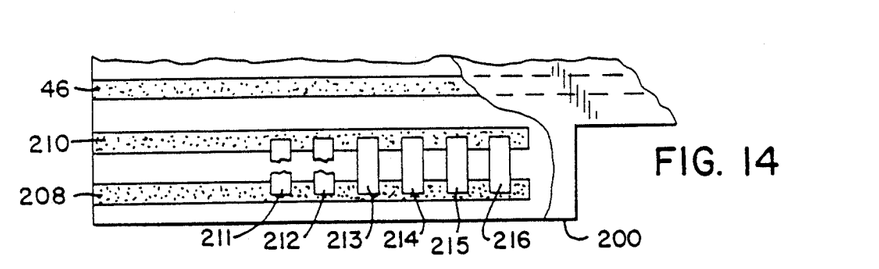
FIG. 14 is a view similar to a portion of FIG. 12 but showing an alternate embodiment.

FIG. 14 shows an alternate embodiment including auxiliary conductors 208 and 210 extending longitudinally along the substrate strip, and resistive material extending laterally therebetween in the form of a plurality of strips 211, 212, 213, 214, 215, 216. The strips are trimmed, e.g. by cutting or otherwise forming a discontinuity therein as at strips 211 and 212, or by reducing their width or thickness, to vary the resistance between auxiliary conductors 208 and 210, and in turn provide encoding means of coded known resistance.

Figure 15:
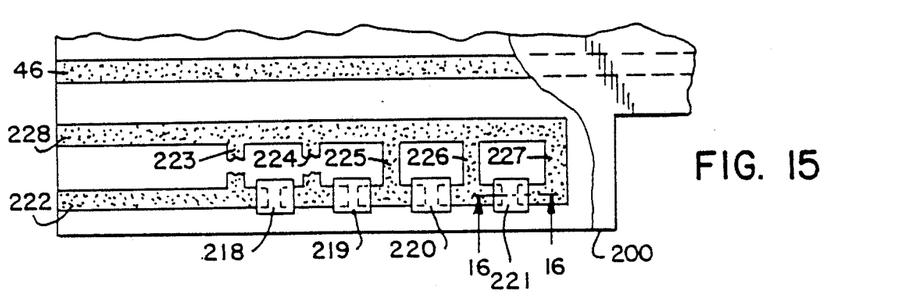
FIG. 15 is a view similar to a portion of FIG. 12 but showing another alternate embodiment.
Figure 16:
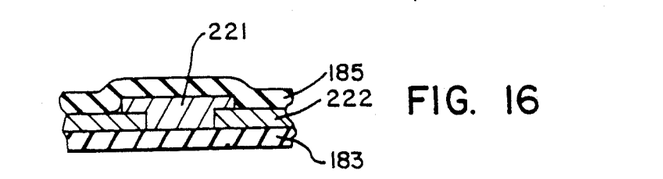
FIG. 16 is a sectional view taken along line 16—16 of FIG. 15.

In another alternative, FIG. 15, the resistive film material is provided by resistive steps 218, 219, 220, 221 formed along auxiliary conductor 222, each step bridging a respective discontinuity in such conductor. A plurality of cross-conductor strips 223, 224, 225, 226, 227 extend laterally between auxiliary conductors 222 and 228 at respective resistive steps. The cross-conductors are trimmed, e.g. by cutting or otherwise forming a discontinuity therein as shown at cross-conductors 223 and 224, or by reducing their width or thickness, to control the number of resistive steps in the circuit between auxiliary conductors 222 and 228 and/or the resistive value thereof, and in turn control resistivity between auxiliary conductors 222 and 228.

The noted auxiliary conductors and resistive material therebetween provide a simple yet effective oximeter encoder particularly suitable for use in combination with the sensor assembly and integral cable of the parent application. Like the parent application oximeter sensor assembly with integral cable, the encoder is characterized by low material cost, low assembly cost, suitability for high volume automated manufacturing as well as variable quantity manufacturing. The assembly with the encoder provides a high degree of mechanical flexibility, and also offers full electromagnetic interference shielding if desired. The various insulating, sealing, and shielding layers as appropriate, are merely widened at portion 200.

It is recognized that various equivalents, alternatives and modifications are possible within the scope of the appended claims. For example, in FIG. 12, the relative position of conductors 202 and 204 an resistance 206 can be varied, as can the shape of end portion 92. In FIGS. 14 and 15, the number of ladder steps is usually chosen according to the number of bins or groups into which the LEDs or optosensors are sorted, for ease of coding, though other numbers of steps may be used.

I claim:

1. An oximeter sensor assembly with integral cable comprising:
    a thin elongated flexible sheet-like electrically insulating substrate strip having an integral end portion capable of flexibly wrapping at least partially around a human body part;
    a plurality of primary electrical conductors on said substrate strip;
    a light emitting electrical component and a light receiving electrical component mounted on said substrate strip at said end portion and electrically connected to respective said primary conductors, said light emitting electrical component emitting light capable of passing through a human body part, said light receiving electrical component receiving said light;
    encoding means on said substrate strip providing signals to the oximeter indicative of the known wavelength of said light emitting electrical component, said encoding means comprising a pair of auxiliary electrical conductors on said substrate strip and means for varying electrical conductivity therebetween comprising thin film resistive material deposited on said substrate between said auxiliary conductors;
    thin elongated sheet-like electrically insulating film means on said substrate strip covering said primary conductors and said encoding means.

2. The invention according to claim 1 wherein:
    at least two of said primary conductors extend along said end portion of said substrate strip to a first given area of said end portion of said substrate strip;
    said light emitting electrical component is mounted on said substrate strip at said first given area and connected to said two primary conductors;
    another two of said primary conductors extend along said end portion of said substrate strip to a second given area of said end portion of said substrate strip;
    said light receiving electrical component is mounted to said substrate strip at said second area and connected to said other two primary conductors;
    said first and second areas of said end portion of said substrate strip are spaced along said end portion and have an intermediate section of said end portion therebetween, said intermediate section capable of flexibly wrapping at least partially around a human body part such that the latter is between said first and second areas of said end portion and between said light emitting electrical component and said light receiving electrical component;
    said substrate strip has a second end portion opposite said first mentioned end portion, said second end portion being at the oximeter, said substrate strip and said primary conductors extending integrally and continuously from said first end portion all the way to said second end portion;
    said auxiliary conductors extend along said second end portion of said substrate strip.

3. The invention according to claim 1 wherein said auxiliary conductors extend longitudinally along said substrate strip, and said thin film resistive material extends laterally therebetween.

4. The invention according to claim 3 wherein said thin film resistive material comprises a plurality of strips extending laterally between said auxiliary conductors, one or more of said strips being trimmed to vary the resistance between said auxiliary conductors.

5. The invention according to claim 1 wherein said thin film resistive material comprises one or more resistive steps formed along one of said auxiliary conductors, and a plurality of cross-strips extending laterally between said auxiliary conductors at respective resistive steps, one or more of said cross-strips being trimmed to control the number of resistive steps in the circuit between said auxiliary conductors and in turn control resistivity between said auxiliary conductors.

6. An oximeter sensor assembly with integral cable comprising:
- a first layer comprising a thin elongated flexible sheet-like electrically insulating strip;
- a second layer on said first layer and comprising a thin elongated flexible sheet-like electrically conductive strip;
- a third layer on said second layer and comprising a thin elongated flexible sheet-like electrically insulating strip;
- a fourth layer on said third layer and comprising a plurality of electrical conductors;
- a fifth layer on said fourth layer and comprising a thin elongated flexible sheet-like electrically insulating strip;
- a sixth layer on said fifth layer and comprising a thin elongated flexible sheet-like electrically conductive strip;
- a seventh layer on said sixth layer and comprising a thin elongated flexible sheet-like electrically insulating strip;
- said third layer having a flexible end portion for flexibly wrapping at least partially around a human body part;
- a light emitting electrical component and a light receiving electrical component mounted on said third layer at said end portion and electrically connected to respective said conductors, said light emitting electrical component emitting light capable of passing through a human body part, said light receiving electrical component receiving said light;
- encoding means providing signals to the oximeter indicative of the known wavelength of said light emitting electrical component, said encoding means comprising a pair of auxiliary electrical conductors on said third layer and means for varying electrical conductivity therebetween comprising thin film resistive material deposited on said third layer between said auxiliary conductors.

7. An oximeter sensor assembly with integral cable comprising:
- a first layer comprising a thin elongated flexible sheet-like electrically insulating strip;
- a second layer on said first layer and comprising a thin elongated flexible sheet-like electrically conductive strip;
- a third layer on said second layer and comprising a thin elongated flexible sheet-like electrically insulating strip;
- a fourth layer on said third layer and comprising a plurality of electrical conductors;
- a fifth layer on said fourth layer and comprising thin elongated flexible sheet-like electrically insulating strip;
- a sixth layer on said fifth layer and comprising thin elongated flexible sheet-like electrically conductive strip;
- a seventh layer on said sixth layer and comprising thin elongated flexible sheet-like electrically insulating strip;
- said third layer having a flexible end portion for flexibly wrapping at least partially around a human body part;
- a light emitting electrical component and a light receiving electrical component mounted on said third layer at said end portion and electrically connected to respective said conductors, said light emitting electrical component emitting light capable of passing through a human body part, said light receiving electrical component receiving said light, wherein:
- said first and seventh layers have lateral widths greater than said second and sixth layers and extend laterally beyond said second and sixth layers;
- said first and seventh layers engage each other along their laterally outward edges;
- said second and sixth layers have lateral widths greater than said third and fifth layers and extend laterally beyond said third and fifth layers;
- said second and sixth layers engage each other along their laterally outward edges and provide electromagnetic interference shielding of said conductors;
- said third and fifth layers extend laterally beyond the lateral extent of said conductors;
- said third and fifth layers engage each other along their laterally outward edges;
- said third and fifth layers have an aligned gap therein having lateral right and left sides and separating one or more said conductors on the lateral right side of said gap, and one or more said conductors on the lateral left side of said gap, and wherein said second and sixth layers engage each other in electrical contact in said gap in addition to engagement of said second and sixth layers along their laterally outward edges, such that the electromagnetic interference shield provided by said second and sixth layers extends around all said conductors and also has a portion extending around and shielding said conductors on said lateral right side of said gap and also has another portion extending around and shielding said conductors on said lateral left side of said gap;
- encoding means on one of said layers providing signals to the oximeter indicative of the known wavelength of said light emitting electrical component.

8. The invention according to claim 7 wherein said encoding means is on said third layer.

9. An oximeter sensor assembly with integral cable comprising:
- a first layer comprising a thin elongated flexible sheet-like electrically insulating strip;
- a second layer on said first layer and comprising a thin elongated flexible sheet-like electrically conductive strip;
- a third layer on said second layer and comprising a thin elongated flexible sheet-like electrically insulating strip;
- a fourth layer on said third layer and comprising a plurality of electrical conductors;

a fifth layer on said fourth layer and comprising a thin elongated flexible sheet-like electrically insulating strip;

a sixth layer on said fifth layer and comprising a thin elongated flexible sheet-like electrically conductive strip;

a seventh layer on said sixth layer and comprising a thin elongated flexible sheet-like electrically insulating strip;

said third layer having a flexible end portion for flexibly wrapping at least partially around a human body part;

a light emitting electrical component and a light receiving electrical component mounted on said third layer at said end portion and electrically connected to respective said conductors, said light emitting electrical component emitting light capable of passing through a human body part, said light receiving electrical component receiving said light, wherein:

said first and seventh layers have lateral widths greater than said second and sixth layers and extend laterally beyond said second and sixth layers;

said first and seventh layers engage each other along their laterally outward edges;

said second and sixth layers have lateral widths greater than said third and fifth layers and extend laterally beyond said third and fifth layers; said second and sixth layers engage each other along their laterally outward edges and provide electromagnetic interference shielding of said conductors;

said third and fifth layers extend laterally beyond the lateral extent of said conductors;

said third and fifth layers engage each other along their laterally outward edges;

wherein said fifth layer has a gap therein having lateral right and left sides and separating one or more said conductors on the lateral right side of said gap, and one or more said conductors on the lateral left side of said gap, and comprising a conductor in said gap and contacted by said sixth layer thereabove, such that said last mentioned conductor is electrically connected to both said second and sixth layers and provides a shield connection to the electromagnetic interference shield provided by said second and sixth layers;

encoding means on one of said layers providing signals to the oximeter indicative of the known wavelength of said light emitting electrical component.

10. The invention according to claim 9 wherein said encoding means is on said third layer.

* * * * *